(12) United States Patent
Köhle et al.

(10) Patent No.: US 8,883,712 B2
(45) Date of Patent: Nov. 11, 2014

(54) FABRIC SOFTENING COMPOSITION

(75) Inventors: Hans-Jürgen Köhle, Mainhausen (DE);
Ulrike Kottke,
Linsengericht-Grossenhausen (DE);
Hans Henning Wenk, Mülheim a. d.
Ruhr (DE); Harald Jakob, Hasselroth
(DE)

(73) Assignee: Evonik Degussa GmbH, Essen (DE)

( * ) Notice: Subject to any disclaimer, the term of this patent is extended or adjusted under 35 U.S.C. 154(b) by 94 days.

(21) Appl. No.: 13/643,486

(22) PCT Filed: Apr. 19, 2011

(86) PCT No.: PCT/EP2011/056185
§ 371 (c)(1),
(2), (4) Date: Oct. 25, 2012

(87) PCT Pub. No.: WO2011/134835
PCT Pub. Date: Nov. 3, 2011

(65) Prior Publication Data
US 2013/0053299 A1 Feb. 28, 2013

(30) Foreign Application Priority Data
Apr. 28, 2010 (EP) .................... 10161296

(51) Int. Cl.
C11D 1/835 (2006.01)
C11D 3/20 (2006.01)
C11D 1/62 (2006.01)
C07C 219/06 (2006.01)
C11D 3/00 (2006.01)
C07C 213/06 (2006.01)
C11D 1/66 (2006.01)

(52) U.S. Cl.
CPC .......... *C11D 1/835* (2013.01); *C11D 1/667* (2013.01); *C11D 3/2079* (2013.01); *C11D 1/62* (2013.01); *C11D 3/2013* (2013.01); *C07C 219/06* (2013.01); *C11D 3/0015* (2013.01); *C07C 213/06* (2013.01)
USPC ........................................ 510/515

(58) Field of Classification Search
USPC .......................... 510/501, 504, 515
See application file for complete search history.

(56) References Cited

U.S. PATENT DOCUMENTS

| 4,234,627 A | 11/1980 | Schilling |
| 4,514,461 A | 4/1985 | Woo |
| 4,747,880 A | 5/1988 | Berrido et al. |
| RE32,713 E | 7/1988 | Woo |
| 4,789,491 A | 12/1988 | Chang et al. |
| 4,882,220 A | 11/1989 | Ono et al. |
| 4,917,920 A | 4/1990 | Ono et al. |
| 4,954,285 A | 9/1990 | Wierenga et al. |
| 5,002,681 A | 3/1991 | Wierenga et al. |
| 5,137,646 A | 8/1992 | Schmidt et al. |
| 5,185,088 A * | 2/1993 | Hartman et al. ............. 510/515 |
| 5,391,325 A | 2/1995 | Swenson et al. |
| 5,427,697 A | 6/1995 | Swartley |
| 5,474,691 A * | 12/1995 | Severns ..................... 510/516 |
| 5,476,599 A * | 12/1995 | Rusche et al. ............... 510/517 |
| 5,480,567 A | 1/1996 | Lam et al. |
| 5,703,029 A | 12/1997 | Crass et al. |
| 5,759,990 A | 6/1998 | Wahl et al. |
| 5,792,219 A | 8/1998 | Hartman et al. |
| 5,827,451 A | 10/1998 | Cummings et al. |
| 5,830,845 A | 11/1998 | Trinh et al. |
| 5,877,145 A | 3/1999 | Wahl et al. |
| 5,916,863 A | 6/1999 | Iacobucci et al. |
| 6,004,913 A | 12/1999 | Iacobucci et al. |
| 6,037,315 A | 3/2000 | Franklin et al. |

(Continued)

FOREIGN PATENT DOCUMENTS

| CA | 1312619 | 1/1993 |
| CS | 246532 | 3/1986 |

(Continued)

OTHER PUBLICATIONS

Akram, et al., "Synthesis of Tallow Based Esterquat," *J. Sci. Res.* vol. XXX(1):31-36 (Jun. 1, 2010).

(Continued)

*Primary Examiner* — John Hardee
(74) *Attorney, Agent, or Firm* — Michael A. Sanzo, LLC

(57) ABSTRACT

A fabric softening composition which comprises as component A a tertiary or quaternary ammonium salt of formulae (I) or (II):

$$R^1R^2R^3N^+CH_2CHR^4OC(=O)R^5X^- \quad (I)$$

$$R^1R^2R^3N^+(CH_2)_3NHR(=O)R^5X^- \quad (II)$$

in which $R^1$ is hydrogen, methyl or ethyl, $R^2$ and $R^3$, independently of one another, are $C_{1-4}$ alkyl or $C_{2-4}$ hydroxyalkyl, $R^4$ is hydrogen or methyl, $R^5$ is a linear $C_{15-21}$ alkyl or alkenyl radical and $X^-$ is a monovalent anion, and as component B a nonionic softener with only one long-chain hydrocarbon radical bonded to a polar radical having at least one free hydroxy group, where fatty alcohol alkoxylate or fatty acid alkoxylate are excluded as component B, exhibits a good softening effect and forms storage-stable dispersions if the molar ratio of component A to component B is in the range from 2:1 to 1:3, the difference between the average chain length of the long-chain hydrocarbon radicals of components A and B is at most 2 carbon atoms and the hydrocarbon radicals of components A and B have on average in each case at most 0.5 double bonds per hydrocarbon radical.

Such a composition can be produced by reacting a fatty acid, a $C_{2-6}$ diol or $C_{3-9}$ polyol, and a tertiary alkanolamine or a diamine having a tertiary and primary amino group in a suitable molar ratio with the removal of water and subsequent alkylation or protonation.

19 Claims, No Drawings

(56) References Cited

U.S. PATENT DOCUMENTS

| | | | |
|---|---|---|---|
| 6,180,593 B1 | 1/2001 | Fender et al. | |
| 6,200,949 B1 | 3/2001 | Reijmer et al. | |
| 6,235,914 B1 | 5/2001 | Steiger et al. | |
| 6,255,274 B1 | 7/2001 | Becherer et al. | |
| 6,376,455 B1 | 4/2002 | Friedli et al. | |
| 6,458,343 B1 | 10/2002 | Zeman et al. | |
| 6,492,322 B1 | 12/2002 | Cooper et al. | |
| 6,608,024 B1 | 8/2003 | DuVal et al. | |
| 6,645,479 B1 | 11/2003 | Shefer et al. | |
| 6,653,275 B1 | 11/2003 | Fender et al. | |
| 6,770,608 B2 | 8/2004 | Franklin et al. | |
| 6,878,684 B2 * | 4/2005 | Ellson et al. | 510/522 |
| 6,897,194 B2 | 5/2005 | Fan et al. | |
| 6,987,074 B2 | 1/2006 | Ishii et al. | |
| 7,572,761 B2 | 8/2009 | Gefvert | |
| 7,704,940 B2 | 4/2010 | Boerefijn et al. | |
| 7,994,110 B2 | 8/2011 | Wenk et al. | |
| 8,183,199 B2 | 5/2012 | Fossum et al. | |
| 8,361,953 B2 | 1/2013 | Nagy et al. | |
| 8,507,425 B2 | 8/2013 | Schick et al. | |
| 8,563,499 B2 | 10/2013 | Köhle et al. | |
| 8,569,224 B2 | 10/2013 | Köhle et al. | |
| 2003/0060390 A1 | 3/2003 | Demeyere et al. | |
| 2003/0158344 A1 | 8/2003 | Rodriques et al. | |
| 2003/0165692 A1 | 9/2003 | Koch et al. | |
| 2003/0195130 A1 | 10/2003 | Lentsch et al. | |
| 2003/0195133 A1 | 10/2003 | Shefer et al. | |
| 2003/0203829 A1 | 10/2003 | Shefer et al. | |
| 2003/0215417 A1 | 11/2003 | Uchiyama et al. | |
| 2003/0216282 A1 | 11/2003 | Martens et al. | |
| 2003/0216488 A1 | 11/2003 | Uchiyama et al. | |
| 2003/0220210 A1 | 11/2003 | DuVal et al. | |
| 2004/0071742 A1 | 4/2004 | Popplewell et al. | |
| 2004/0071746 A1 | 4/2004 | Popplewell et al. | |
| 2004/0072719 A1 | 4/2004 | Bennett et al. | |
| 2004/0072720 A1 | 4/2004 | Brain et al. | |
| 2004/0087477 A1 | 5/2004 | Ness | |
| 2004/0106536 A1 | 6/2004 | Mane et al. | |
| 2004/0167056 A1 | 8/2004 | Lentsch et al. | |
| 2004/0204337 A1 | 10/2004 | Corona et al. | |
| 2005/0014672 A1 | 1/2005 | Arif | |
| 2005/0032671 A1 | 2/2005 | Kvita et al. | |
| 2006/0089293 A1 | 4/2006 | Frankenbach | |
| 2006/0094639 A1 | 5/2006 | Martin et al. | |
| 2006/0142175 A1 | 6/2006 | Haiss et al. | |
| 2006/0252669 A1 | 11/2006 | Heibel et al. | |
| 2006/0277689 A1 | 12/2006 | Hubig et al. | |
| 2007/0054835 A1 | 3/2007 | Corona et al. | |
| 2007/0066510 A1 | 3/2007 | Tee et al. | |
| 2007/0219111 A1 | 9/2007 | Ward et al. | |
| 2008/0242584 A1 | 10/2008 | Wahl et al. | |
| 2008/0263780 A1 | 10/2008 | Declercq et al. | |
| 2008/0289116 A1 | 11/2008 | Young et al. | |
| 2009/0124533 A1 | 5/2009 | Kottke et al. | |
| 2009/0181877 A1 | 7/2009 | McGinnis et al. | |
| 2009/0203571 A1 | 8/2009 | Nagy et al. | |
| 2011/0110993 A1 | 5/2011 | Chieffi et al. | |
| 2011/0239377 A1 | 10/2011 | Fossum et al. | |
| 2011/0239378 A1 | 10/2011 | Fossum et al. | |
| 2011/0245138 A1 | 10/2011 | Köhle et al. | |
| 2011/0245139 A1 | 10/2011 | Köhle et al. | |
| 2011/0245140 A1 | 10/2011 | Demeyere | |
| 2012/0021959 A1 | 1/2012 | Morgan, III et al. | |
| 2012/0088712 A1 | 4/2012 | Schick et al. | |
| 2013/0196894 A1 | 8/2013 | Parrish et al. | |

FOREIGN PATENT DOCUMENTS

| | | |
|---|---|---|
| DE | 24 30 140 A1 | 2/1976 |
| DE | 34 02 146 A1 | 7/1985 |
| DE | 36 08 093 A1 | 9/1987 |
| DE | 197 08 133 | 12/1997 |
| EP | 0 284 036 | 9/1988 |
| EP | 0 293 955 A2 | 12/1988 |
| EP | 0 302 567 A2 | 2/1989 |
| EP | 0 421 146 A2 | 9/1990 |
| EP | 0 829 531 A1 | 3/1998 |
| EP | 1 018 541 A1 | 7/2000 |
| EP | 1 323 817 A1 | 12/2001 |
| EP | 1 393 706 A1 | 3/2004 |
| EP | 1 584 674 A1 | 10/2005 |
| EP | 1 840 197 A1 | 2/2007 |
| EP | 1 806 392 A1 | 7/2007 |
| GB | 2 007 734 A | 5/1979 |
| GB | 2 039 556 | 8/1980 |
| WO | WO 91/01295 | 2/1991 |
| WO | WO 92/18593 | 10/1992 |
| WO | WO 94/14935 | 7/1994 |
| WO | WO 94/19439 | 9/1994 |
| WO | WO 97/42279 | 11/1997 |
| WO | WO 98/38277 | 9/1998 |
| WO | WO 00/06678 | 2/2000 |
| WO | WO 01/32813 A1 | 5/2001 |
| WO | WO 2005/085404 A1 | 9/2005 |
| WO | WO 2007/026314 A2 | 3/2007 |
| WO | WO 2007/125005 | 11/2007 |
| WO | WO 2008/003454 A1 | 1/2008 |
| WO | WO 2008/104509 | 9/2008 |
| WO | WO 2009/018955 A2 | 2/2009 |
| WO | WO 2009/099618 A1 | 8/2009 |
| WO | WO 2011/120836 A1 | 10/2011 |
| WO | WO 2011/123284 A1 | 10/2011 |
| WO | WO 2011/123606 A1 | 10/2011 |
| WO | WO 2011/123733 A1 | 10/2011 |

OTHER PUBLICATIONS

U.S. Appl. No. 13/754,266, filed Jan. 30, 2013, Parrish, et al.
English translation of the International Search Report for PCT/EP2011/056185 filed Apr. 19, 2011.
English translation of the Written Opinion of the International Searching Authority for PCT/EP2011/056185 filed Apr. 19, 2011.
English translation of the International Preliminary Report on Patentability for PCT/EP2011/056185 filed Apr. 19, 2011.
English language translation of CS 246532.
English language abstract for DE 24 30 140.
English language abstract for DE 34 02 146 A1.
English language abstract for DE 36 08 093.
English language abstract for DE 197 08 133.
English language abstract for EP 0 284 036.
English language abstract for EP 0 421 146 A2.
English language abstract for EP 1 018 541.
English language abstract for EP 1 323 817 A1.
English language abstract for WO 91/01295.
English language abstract for WO 94/14935.
English language abstract for WO 2007/125005.
English language abstract for WO 2009/018955 A2.
Second English language abstract for WO 2009/018955 A2.
Price-Jones, et al., "N,N'-ethylenediyl-*bis*-alkanamides: Differential scanning calorimetry studies," *J. Am. Oil Chem. Soc.* 73:311-319 (1996).
Product Advertisement for Tetranyl AO-1, http//kaochemicals-eu.com/213.html, downloaded Jul. 27, 2011.
Ullman's Encyclopedia of Industrial Chemistry; Wiley-VCH Verlag GmbH & Co. KGaA, Weinheim, vol. 14, Table 2, p. 77 (2012).
U.S. Appl. No. 13/603,000, filed Sep. 4, 2012, Nagy.

* cited by examiner

FABRIC SOFTENING COMPOSITION

CROSS REFERENCE TO RELATED APPLICATIONS

The present application is US national stage of international application PCT/EP2011/056185, which had an international filing date of Apr. 19, 2011, and which was published in German under on Nov. 3, 2011. Priority is claimed to European application EP 10161296.8, filed on Apr. 28, 2010.

The invention relates to a fabric softening composition, to a process for producing such a composition, to the use of the composition for producing an aqueous rinse cycle fabric softener and to an aqueous rinse cycle fabric softener comprising the composition.

Quaternary ammonium salts carrying two long-chain hydrocarbon radicals are normally used as the fabric softening compound for producing aqueous rinse cycle fabric softeners. Such quaternary ammonium salts allow for the production of stable aqueous dispersions which are suitable as rinse cycle fabric softeners and which achieve a good softening effect. However, a disadvantage is the sensitivity of these active ingredients to anionic surfactants, the presence of which adversely affects the softening effect. There is therefore a need for alternative fabric softening active ingredients whose softening effect is less adversely affected by anionic surfactants.

WO 92/18593 describes particulate fabric softening compositions which comprise a nonionic softener and a cationic surfactant with only one long-chain $C_{12-30}$ hydrocarbon radical. The nonionic softener is not substantive, i.e. it is not deposited from an aqueous dispersion onto a fabric and can therefore not be used in its own right in an aqueous rinse cycle fabric softener. Although the cationic surfactant with only one long-chain $C_{12-30}$ hydrocarbon radical is substantive, it does not have a fabric softening effect. The combination of the two components acts synergistically by the cationic surfactant depositing the nonionic softener from aqueous dispersion onto a fabric. According to the teaching of WO 92/18593, the particulate fabric softening composition is dispersed in water directly prior to use. The fabric softening compositions described in the examples of WO 92/18593, however, are unsuitable for producing aqueous rinse cycle fabric softeners since the dispersions obtainable therefrom are not sufficiently storage-stable. Moreover, they also have an inadequate softening effect.

EP 0 284 036 describes a process for producing quaternized alkanolamine fatty acid esters in which a triglyceride is transesterified with an alkanolamine and the resulting reaction mixture is quaternized. EP 0 284 036 teaches the use of a molar ratio of 1 mol of glyceride to 3 mol of alkanolamine for producing monoesters. The compositions obtained thereby comprise a quaternary ammonium salt with a long-chain hydrocarbon radical and a glycerol fatty acid monoester in a molar ratio of more than 2.5:1 and have an inadequate softening effect.

CS 246 532 describes fabric softening compositions which comprise a synergistic mixture of a choline fatty acid ester and a fatty alcohol ethoxylate in a molar ratio of 0.1:1 to 8:1 and are derived from fatty acids having 8 to 23 carbon atoms. However, the softening effect of these compositions is unsatisfactory.

GB 2 039 556 describes fabric softening compositions which comprise 20 to 95 mol % of a cationic surfactant with two $C_{12-22}$ hydrocarbon radicals and 5 to 80 mol % of a $C_{8-24}$ fatty acid and which can additionally comprise up to 50 mol % of a cationic surfactant with only one $C_{10-24}$ hydrocarbon radical. According to the teaching of GB 2 039 556, the cationic surfactant with two hydrocarbon radicals is a necessary component of the composition and, in the explicitly disclosed compositions, the molar fraction of cationic surfactant with two hydrocarbon radicals is always at least as high as the molar fraction of cationic surfactant with one hydrocarbon radical.

However, compared to the customary quaternary ammonium salts with two long-chain hydrocarbon radicals, all of the compositions known from the prior art which combine a nonionic softener and a cationic surfactant with only one long-chain hydrocarbon radical have the disadvantage that they do not achieve a comparably high softening effect and in most cases also do not produce sufficiently storage-stable aqueous dispersions.

Surprisingly, it has now been found that for compositions, combining a nonionic softener and a cationic surfactant with only one long-chain hydrocarbon radical, simultaneous achievement of a high softening effect and of a good storage stability of an aqueous dispersion depends essentially on combining a nonionic softener of suitable structure and a tertiary or quaternary ammonium salt in the correct molar ratio and on matching the chain length of the hydrocarbon radicals of both components.

The invention therefore provides a fabric softening composition which comprises as component A at least one tertiary or quaternary ammonium salt selected from compounds of the formulae (I) and (II):

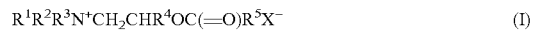

$$R^1R^2R^3N^+CH_2CHR^4OC(=O)R^5 X^- \quad (I)$$

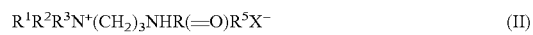

$$R^1R^2R^3N^+(CH_2)_3NHR(=O)R^5 X^- \quad (II)$$

in which $R^1$ is hydrogen, methyl or ethyl,
$R^2$ and $R^3$, independently of one another, are $C_{1-4}$ alkyl or $C_{2-4}$ hydroxyalkyl,
$R^4$ is hydrogen or methyl,
$R^5$ is a linear $C_{15-21}$ alkyl or alkenyl radical and
$X^-$ is a monovalent anion,
and as component B at least one nonionic softener which has only one long-chain hydrocarbon radical having 15 to 21 carbon atoms bonded to a polar radical, where the polar radical comprises at most 9 carbon atoms and carries at least one free hydroxy group and where the nonionic softener is not a fatty alcohol alkoxylate or fatty acid alkoxylate, and for which
i) the molar ratio of the total amount of component A to the total amount of component B is in the range from 2:1 to 1:3,
ii) the difference between the average chain length of the long-chain hydrocarbon radicals of components A and B is at most 2 carbon atoms,
iii) the hydrocarbon radicals of components A and B have on average in each case at most 0.5 double bonds per hydrocarbon radical and
iv) the total amount of tertiary and quaternary ammonium salts, carrying two long-chain hydrocarbon radicals of 15 to 21 carbon atoms, in the composition is at most 80 mol % and preferably at most 50 mol % of the total amount of components A.

Moreover, the invention provides the use of a fabric softening composition according to the invention for producing an aqueous rinse cycle fabric softener, and also an aqueous rinse cycle fabric softener which comprises 2 to 25% by weight of such fabric softening composition and 70 to 98% by weight of water.

The invention further provides two alternative processes for producing fabric softening compositions according to the invention.

The first process comprises the reaction of a mixture comprising n mol of a $C_{16-22}$ fatty acid with an iodine number of at most 45, m mol of a $C_{2-6}$ diol or $C_{3-9}$ polyol and p mol of an alkanolamine of the formula $R^2R^3NCH_2CHR^4OH$, in which $R^2$ and $R^3$, independently of one another, are methyl, 2-hydroxyethyl or 2-hydroxypropyl and $R^4$ is hydrogen or methyl, where the ratio of p:m is in the range from 2:1 to 1:3 and n:(p+m) is in the range from 0.75 to 1.4, at a temperature in the range from 140 to 210° C. with removal of water and a subsequent reaction of the mixture obtained in step a) with an alkylating agent at a temperature in the range from 50 to 100° C. until at least 90% of the tertiary amino groups have been quaternized, or with an acid until at least 98% of the tertiary amino groups have been protonated.

The second process comprises the reaction of a mixture comprising n mol of a $C_{16-22}$ fatty acid with an iodine number of at most 45, m mol of a $C_{2-6}$ diol or $C_{3-9}$ polyol and p mol of N,N-dimethyl-1,3-propanediamine, where the ratio of p:m is in the range from 2:1 to 1:3 and n is in the range from 0.75*m+p to 1.4*m+p, at a temperature in the range from 140 to 210° C. with removal of water and a subsequent reaction of the mixture obtained in step a) with an alkylating agent at a temperature in the range from 50 to 100° C. until at least 90% of the tertiary amino groups have been quaternized, or with an acid until at least 98% of the tertiary amino groups have been protonated.

The fabric softening composition according to the invention comprises, as component A, at least one tertiary or quaternary ammonium salt and, as component B, at least one nonionic softener.

In the fabric softening composition according to the invention, the component A is selected from compounds of the formulae (I) and (II):

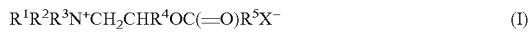

$$R^1R^2R^3N^+CH_2CHR^4OC(=O)R^5X^- \quad (I)$$

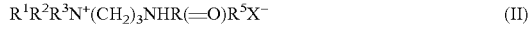

$$R^1R^2R^3N^+(CH_2)_3NHR(=O)R^5X^- \quad (II)$$

in which $R^1$ is hydrogen, methyl or ethyl, $R^2$ and $R^3$, independently of one another, are $C_{1-4}$ alkyl or $C_{2-4}$ hydroxyalkyl, $R^4$ is hydrogen or methyl, $R^5$ is a linear $C_{15-21}$ alkyl or alkenyl radical and $X^-$ is a monovalent anion.

The tertiary or quaternary ammonium salts of component A have only one long-chain hydrocarbon radical which comprises 15 to 21 carbon atoms. The long-chain hydrocarbon radical is preferably unbranched. Tertiary or quaternary ammonium salts in which a fatty acid radical is bonded to the nitrogen atom via an ester group or amide group and a linking group having two or three carbon atoms have a better biodegradability compared with tertiary or quaternary ammonium salts in which a long-chain hydrocarbon radical is bonded directly to the nitrogen atom of the ammonium salt. Preferably, the long-chain hydrocarbon radical contains at most one double bond in order to avoid oxidation during storage.

The other groups bonded to the nitrogen atom of the tertiary or quaternary ammonium salt in each case have fewer carbon atoms and, besides a hydrogen atom in the case of a tertiary ammonium salt, are preferably short-chain groups having in each case fewer than 4 carbon atoms and particularly preferably, independently of one another, are methyl, ethyl or hydroxyethyl.

In a preferred embodiment, in the formulae (I) and (II), $R^2$ is a $C_{1-4}$ alkyl radical, preferably a methyl radical. Particularly preferably, $R^2$ and $R^3$, independently of one another, are $C_{1-4}$ alkyl radicals and preferably methyl radicals.

In a further preferred embodiment, in formula (I), $R^1$ is methyl, $R^2$ and $R^3$, independently of one another, are methyl, 2-hydroxyethyl or 2-hydroxypropyl and $X^-$ is chloride or methylsulphate and, in formula (II), $R^1$, $R^2$ and $R^3$ are methyl and $X^-$ is chloride or methylsulphate. Particularly preferably, in formula (I) $R^2$ is a methyl radical and most preferably, in formula (I) $R^2$ and $R^3$ are methyl radicals.

The anion $X^-$ is particularly preferably methylsulphate.

Examples of preferred quaternary ammonium salts of component A are choline methylsulphate hexadecanoic acid ester, choline methylsulphate octadecanoic acid ester, (2-hydroxypropyl)trimethylammonium methyl sulphate hexadecanoic acid ester, (2-hydroxypropyl)trimethylammonium methylsulphate octadecanoic acid ester, bis(2-hydroxyethyl)dimethylammonium methylsulphate hexadecanoic acid monoester, bis(2-hydroxyethyl)-dimethylammonium methylsulphate octadecanoic acid monoester, bis(2-hydroxypropyl)dimethylammonium methylsulphate hexadecanoic acid monoester, bis(2-hydroxypropyl)dimethylammonium methylsulphate octadecanoic acid monoester, tris(2-hydroxyethyl)-methylammonium methylsulphate hexadecanoic acid monoester, tris(2-hydroxyethyl)methylammonium methylsulphate octadecanoic acid monoester, (3-aminopropyl)trimethylammonium methylsulphate hexadecanoic acid amide and (3-aminopropyl)trimethylammonium methylsulphate octadecanoic acid amide.

The fabric softening composition according to the invention comprises, as component B, at least one nonionic softener which has only one long-chain hydrocarbon radical having 15 to 21 carbon atoms bonded to a polar radical. The polar radical comprises at most 9 carbon atoms and carries at least one free hydroxy group. However, the nonionic softener must not be a fatty alcohol alkoxylate or fatty acid alkoxylate since with the combination of such an ethoxylate with a component A only an inadequate softening effect is achieved. Fatty alcohol alkoxylates and fatty acid alkoxylates excluded from the invention are compounds of the formulae (III) and (IV)

$$R^5-(OCH_2CHR^6)_n-OH \quad (III)$$

$$R^5-C(=O)(OCH_2CHR^6)_n-OH \quad (IV)$$

in which $R^5$ is a long-chain hydrocarbon radical having 15 to 21 carbon atoms, $R^6$ is hydrogen or an alkyl radical and n is an integer from 1 to 4.

Preferably, the polar radical comprises at most 6 carbon atoms and particularly preferably at most 3 carbon atoms. The ratio of carbon atoms to free hydroxy groups in the polar radical is preferably not greater than 3. Free hydroxy groups for the purposes of the invention include both alcoholic hydroxy groups which are bonded to a saturated carbon atom, and carboxylic hydroxy groups which are bonded to a carbonyl carbon atom.

In a preferred embodiment, the component B is selected from fatty acids, monoesters of fatty acids with a $C_{2-6}$ diol or $C_{3-9}$ polyol and monoesters of fatty alcohols with a $C_{2-6}$ hydroxycarboxylic acid. Suitable as $C_{2-6}$ diol are here, for example, ethylene glycol, diethylene glycol, 1,2-propanediol, 1,3-propanediol and dipropylene glycol. Suitable as $C_{3-9}$ polyol are, for example, glycerol, diglycerol, triglycerol, sorbitol and sorbitan. Suitable as $C_{2-6}$ hydroxycarboxylic acid are, for example, hydroxyacetic acid, lactic acid and malic acid.

Particularly preferably, the component B is selected from fatty acids and fatty acid monoesters of glycerol, diglycerol, triglycerol, sorbitol and sorbitan.

Examples of particularly preferred nonionic softeners of component B are hexadecanoic acid, octadecanoic acid, glycerol monohexadecanoate, glycerol monooctadecanoate, diglycerol monohexadecanoate, diglycerol monooctadecanoate, triglycerol monohexadecanoate, triglycerol monooctadecanoate, sorbitol monohexadecanoate, sorbitol monooctadecanoate, sorbitan monohexadecanoate and sorbitan monooctadecanoate.

For the purposes of the invention, fatty acids are unbranched alkyl- and alkenylmonocarboxylic acids. For the purposes of the invention, the term fatty acid includes here not only pure substances, but also mixtures of fatty acids of different chain length and mixtures of saturated fatty acids, such as palmitic acid and stearic acid, and unsaturated fatty acids, such as oleic acid and elaidic acid. Preferred fatty acids are mixtures of alkyl- and alkenylmonocarboxylic acids from animal and plant sources, such as, for example, tallow fatty acid, hydrogenated tallow fatty acid, palm fatty acid, hydrogenated canola fatty acid, hydrogenated soy fatty acid, hydrogenated sunflower fatty acid, and mixtures of these fatty acids.

The fabric softening composition according to the invention comprises the components A and B in a molar ratio of the total amount of component A to the total amount of component B in the range from 2:1 to 1:3 and preferably in the range from 1.5:1 to 1:1.5. Observing the ratio according to the invention for components A and B is essential for achieving a high softening effect.

The difference between the average chain length of the long-chain hydrocarbon radicals of components A and B of the fabric softening composition according to the invention must be at most 2 carbon atoms and is preferably at most 1.5 carbon atoms. The term chain length of the long-chain hydrocarbon radical refers here not to the total number of carbon atoms in the hydrocarbon radical, but to the longest chain of carbon atoms present in the hydrocarbon radical. In the case of mixtures of components A or components B with hydrocarbon radicals of different length, the average chain length is calculated from the respective molar fraction of the individual compounds and their chain length. A mixture of 25 mol % of a quaternary ammonium salt with a linear $C_{16}$ hydrocarbon radical and 75 mol % of a quaternary ammonium salt with a linear $C_{18}$ hydrocarbon radical accordingly has an average chain length of 17.5. A difference in the average chain length of more than 2 carbon atoms leads to a reduced softening effect and a poorer storage stability of aqueous dispersions of the composition.

Preferably, the components A and B comprise the same long-chain hydrocarbon radical. This can be achieved for example by preparing the components A and B starting from the same fatty acid or fatty acid mixture.

In the fabric softening composition according to the invention, both the hydrocarbon radicals of components A and also the hydrocarbon radicals of components B must on average have at most 0.5 double bonds per hydrocarbon radical. In the case of mixtures of components A or of components B with different hydrocarbon radicals, the average number of double bonds per hydrocarbon radical is calculated from the respective molar fraction of the individual compounds. A mixture of 75 mol % of a nonionic softener with a saturated stearyl radical and 25 mol % of a nonionic softener with a monounsaturated oleyl radical accordingly has on average 0.25 double bonds per hydrocarbon radical. If the components A or the components B have more than 0.5 double bonds per hydrocarbon radical, the composition exhibits an unsatisfactory softening effect and aqueous dispersions of the composition have an inadequate storage stability.

In the case of fabric softening compositions whose components A or components B are derived from a fatty acid mixture, the components are preferably derived from a fatty acid mixture with an iodine number of at most 45 and particularly preferably at most 25.

In the fabric softening composition according to the invention, the total amount of tertiary and quaternary ammonium salts which have two long-chain hydrocarbon radicals having 15 to 21 carbon atoms is at most 80 mol % of the total amount of components A, preferably at most 50 mol % of the total amount of components A and particularly preferably at most 20 mol % of the total amount of components A. The molar ratio of the total amount of tertiary and quaternary ammonium salts which have only one long-chain hydrocarbon radical having 15 to 21 carbon atoms relative to the amount of tertiary and quaternary ammonium salts which have two long-chain hydrocarbon radicals having 15 to 21 carbon atoms is accordingly at least 1:0.8, preferably at least 1:0.5 and particularly preferably at least 1:0.2. Limiting the fraction of quaternary ammonium salts with two long-chain hydrocarbon radicals allows the softening effect of the composition to be improved, especially in the presence of anionic surfactants.

A preferred embodiment of the fabric softening composition according to the invention is a concentrated composition in which the total fraction of components A and components B in the composition is at least 50% by weight and preferably at least 80% by weight. The concentrated compositions have the advantage that in liquid form they are self-dispersing upon addition to water or an aqueous solution, i.e. they form finely distributed storage-stable dispersions even without the action of strong shear forces, whereas in the case of separate additions of components A and B to water or an aqueous solution high shear forces are required in order to obtain dispersions which can be used as rinse cycle fabric softeners.

In addition to the components A and B, the concentrated compositions according to the invention can also comprise one or more solvents in a total amount of up to 20% by weight. Suitable solvents are ethanol, 2-propanol, glycerol, ethylene glycol, 1,2-propylene glycol, dipropylene glycol and C1-C4 alkyl monoethers of ethylene glycol, 1,2-propylene glycol and dipropylene glycol, such as, for example, 2-methoxyethanol, 2-ethoxyethanol, 2-butoxyethanol, 1-methoxy-2-propanol, dipropylene glycol monomethyl ether and dipropylene glycol monobutyl ether. Particularly preferred solvents are ethanol and 2-propanol. Likewise suitable as solvents are fatty acid triglycerides with an average chain length of the fatty acid radical of 10 to 14 carbon atoms and an iodine number of 0 to 15, calculated for the free fatty acid, in a total amount of from 2 to 8% by weight, based on the total amount of the composition.

The concentrated compositions according to the invention preferably comprise at most 10% by weight of water and particularly preferably at most 2% by weight of water. With the concentrated compositions according to the invention, higher water contents lead to undesirably high viscosities of the molten composition and can lead to the undesired hydrolysis of the ester group during the storage or handling of the concentrated composition with compositions comprising a fatty acid radical bonded via an ester group in the components A or B.

The fabric softening compositions according to the invention can be produced by mixing at least one tertiary or quaternary ammonium salt having the properties according to the invention and at least one nonionic softener having the properties according to the invention in the molar ratio according to the invention. Suitable tertiary or quaternary ammonium salts and suitable nonionic softeners are commercially available.

However, the fabric softening compositions are preferably produced by the process according to the invention in which a fatty acid, a $C_{2-6}$ diol or $C_{3-9}$ polyol, and also a tertiary alkanolamine or a diamine having tertiary and primary amino group are reacted in a suitable molar ratio with the removal of water and are then alkylated or protonated.

In a first embodiment, the process according to the invention for producing the fabric softening composition comprises, in the first step, the reaction of a mixture comprising a $C_{16-22}$ fatty acid with an iodine number of at most 45, a $C_{2-6}$ diol or $C_{3-9}$ polyol, and also an alkanolamine of the formula $R^2R^3NCH_2CHR^4OH$, in which $R^2$ and $R^3$, independently of one another, are methyl, 2-hydroxyethyl or 2-hydroxypropyl and $R^4$ is hydrogen or methyl. In the process, n mol of fatty acid, m mol of diol or polyol and p mol of alkanolamine are reacted with one another, where the ratio of p to m is in the range from 2:1 to 1:3 and the ratio of n to (p+m) is in the range from 0.75 to 1.4 and preferably in the range from 0.8 to 1.2. The reaction is carried out at a temperature in the range from 140 to 210° C. with the removal of water. The water is removed from the mixture here preferably by distillation. During the reaction, the pressure is preferably reduced from ambient pressure to a pressure in the range from 5 to 100 mbar in order to intensify the removal of water. The reaction can be carried out in the presence of an acid catalyst, which is preferably added in an amount of 0.05 to 0.2% by weight. Suitable acid catalysts are methanesulphonic acid, p-toluenesulphonic acid and hypophosphorous acid. The reaction in the first step is preferably carried out until the acid number of the mixture is in the range from 1 to 10 mg KOH/g.

In a subsequent second step, the mixture obtained in the first step is either quaternized with an alkylating agent or protonated with an acid. In the case of reaction with an alkylating agent, the reaction is carried out at a temperature in the range from 50 to 100° C. until at least 90% of the tertiary amino groups have been quaternized. The alkylating agent used is preferably dimethyl sulphate or methyl chloride and particularly preferably dimethyl sulphate. The alkylating agent is preferably used in an amount of from 0.90 to 0.97 mol and preferably from 0.92 to 0.95 mol of alkylating agent per mole of alkanolamine used. In the case of reaction with an acid, the reaction is carried out until at least 98% of the tertiary amino groups have been protonated. The acids used are preferably carboxylic acids having one to three carbon atoms, preferably formic acid, acetic acid, glycolic acid or lactic acid and particularly preferably acetic acid. For this purpose, the acid is preferably used in an amount of from 0.98 to 1.2 mol and preferably from 1.0 to 1.1 mol of acid per mole of alkanolamine used.

In a second embodiment, the process according to the invention for producing the fabric softening composition comprises, in the first step, the reaction of a mixture comprising a $C_{16-22}$ fatty acid with an iodine number of at most 45, a $C_{2-6}$ diol or $C_{3-9}$ polyol, and also N,N-dimethyl-1,3-propanediamine. In the process, n mol of fatty acid, m mol of diol or polyol and p mol of diamine are reacted with one another, where the ratio of p to m is in the range from 2:1 to 1:3 and n is in the range from 0.75*m+p to 1.4*m+p. The molar amount of fatty acid is accordingly chosen such that it corresponds to the molar amount of diamine plus 0.7 times to 1.4 times the molar amount of diol or polyol. Preferably, n is in the range from 0.8*m+p to 1.2*m+p. The reaction is carried out in the first step under the same conditions as for the first embodiment of the process according to the invention and can be carried out in a similar way in the presence of an acid catalyst. The second step of the process is carried out for the second embodiment of the process according to the invention in the same way as for the first embodiment of the process according to the invention.

In both embodiments, the process according to the invention has the advantage that both components A and B of the composition according to the invention can be produced in the required ratio from low-cost and readily available starting materials using just one reactor. This therefore makes the compositions according to the invention accessible on an industrial scale with low raw material costs and capital costs.

The mixtures obtainable with the process according to the invention are particularly preferred embodiments of the composition according to the invention.

The fabric softening compositions according to the invention and in particular the compositions accessible with the process according to the invention can advantageously be used for producing an aqueous rinse cycle fabric softener since they form storage-stable aqueous dispersions with multilamellar vesicles and, when using a dilute dispersion as rinse cycle fabric softener, they have a good softening effect on textiles which is as high as the softening effect of the customarily used quaternary ammonium salts having two long-chain hydrocarbon radicals. Surprisingly, aqueous rinse cycle fabric softeners with an improved softening effect can be obtained by using a fabric softening composition according to the invention for producing an aqueous rinse cycle fabric softener as compared with a separate addition of the components ammonium salt and nonionic softener.

The aqueous rinse cycle fabric softeners according to the invention comprise 2 to 25% by weight of a fabric softening composition according to the invention and 70 to 98% by weight of water. Preferably, the rinse cycle fabric softeners according to the invention comprise a fabric softening composition obtainable by the process according to the invention.

In addition to the fabric softening composition according to the invention and water, the rinse cycle fabric softeners according to the invention can comprise further additives and auxiliaries, in particular perfume, dye, viscosity regulators, antifoam, preservative and organic solvents.

Perfumes which can be used are all fragrances or fragrance mixtures known to be suitable from the prior art for aqueous rinse cycle fabric softeners, preferably in the form of a perfume oil. Examples of suitable commercial perfume oils are Skyline DW 10557 (manufacturer Symrise), White Blossoms DW 10261/7 (manufacturer Symrise), Refresh 154 (manufacturer IFF Inc.) and Passionflower PCMf (manufacturer Dullberg Konzentra GmbH). Preferably, perfume is used in an amount of from 0.1 to 2% by weight.

Dyes which can be used are all dyes known to be suitable from the prior art for aqueous rinse cycle fabric softeners, with water-soluble dyes being preferred. Examples of suitable standard commercial dyes are SANDOLAN® Milling Blue NBL 150 (manufacturer Clariant), SANDOLAN® Milling Green N-6GL (manufacturer Clariant) and Sicovit® Azorubin 85 E122 (manufacturer BASF). Preferably, dye is used in a weight fraction of from 2 to 100 ppm.

As viscosity regulator for reducing the viscosity, the aqueous rinse cycle fabric softener may comprise an alkali metal salt or alkaline earth metal salt, preferaly calcium chloride, in an amount of from 0.05 to 2% by weight. As viscosity regulator for increasing the viscosity, the aqueous rinse cycle fabric softener may comprise a thickener known to be suitable from the prior art, preference being given to the polyurethane thickeners known from WO 2007/125005. Examples of suitable thickeners are TEGO® Visco Plus 3030 (manufacturer Evonik Tego Chemie), Acusol® 880 and 882 (manufacturer Rohm & Haas), Rheovis® CDE (manufacturer BASF), Rohagit® KF 720 F (manufacturer Evonik Röhm GmbH) and Polygel K100 from Neochem GmbH. Viscous embodiments of the rinse cycle fabric softeners according to the invention preferably comprise a thickener in an amount of from 0.01 to 2% by weight.

Antifoams which can be used are all antifoams known to be suitable from the prior art for aqueous rinse cycle fabric softeners. Examples of suitable standard commercial antifoams are Dow Corning® DB-110A and TEGO® Antifoam 7001 XP. Preferably, antifoam is used in a weight fraction of from 10 to 100 ppm.

As preservative, the aqueous rinse cycle fabric softener may comprise bactericidal and/or fungicidal active ingredients known to be suitable from the prior art, preference being given to water-soluble active ingredients. Examples of suitable commercial bactericides are methylparaben, 2-bromo-2-nitro-1,3-propanediol, 2-methyl-4-isothiazolin-3-one and 5-chloro-2-methyl-4-isothiazolin-3-one. The aqueous rinse cycle softener can likewise comprise an oxidation inhibitor as preservative. Examples of suitable commercial oxidation inhibitors are ascorbic acid, 2,6-di-tert-butyl-4-methylphenol (BHT), butylhydroxyanisole (BHA), tocopherol and propyl gallate. Preferably, bactericides are used in a weight fraction of from 1 to 2000 ppm and oxidation inhibitors are used in a weight fraction of from 10 to 100 ppm.

As organic solvents, the rinse cycle fabric softener may comprise short-chain alcohols, glycols and glycol monoethers, preference being given to ethanol, 2-propanol, 1,2-propanediol and dipropylene glycol. Preferably, organic solvent is used in an amount of from 0.2 to 2% by weight.

The aqueous rinse cycle fabric softeners according to the invention are preferably produced by adding a composition according to the invention in liquid form to water or an aqueous solution. The addition takes place here preferably with stirring or continuously with a static mixer. The composition according to the invention is preferably added at a temperature of at most 80° C., particularly preferably at most 75° C. During the addition the temperature of the water or of the aqueous solution is preferably 10 to 15° C. lower than the temperature of the composition according to the invention. The additives and auxiliaries specified above can be added to the aqueous solution either prior to adding the composition according to the invention, or can be added to the dispersion obtained after adding the composition according to the invention.

The invention is illustrated by the examples and comparative examples below, although these are not intended to limit the subject matter of the invention.

Examples

Preparation of the Compositions

The ammonium salt and the nonionic compound were, if necessary, melted separately, weighed in liquid form into a 50 ml centrifuge tube made of polypropylene in accordance with the desired molar ratio and mixed by shaking using a vortex mixer.

Preparation of a 5% by Weight Aqueous Dispersion:

5 parts of the liquid composition heated to 40 to 80° C. were added with stirring to 95 parts of tap water heated to 45 to 65° C., stirred for 20 min using a propeller stirrer at 45 to 65° C. and cooled to room temperature over the course of ca. one hour.

Determination of the Softening Effect:

The softening effect of the compositions was determined in a sensory test which was carried out by a group of subjects on pieces of terry cotton hand towels which had been treated with an aqueous dispersion of the composition. Terry cotton hand towels measuring 80 cm×50 cm were washed twice using standard detergent powder, rinsed twice and spun and dried in air hanging on a line. A 5% by weight aqueous dispersion of the composition prepared as described above was diluted with cold tap water to give a rinse solution comprising 0.025% by weight of the composition. The terry cotton hand towels were immersed for 10 min in 2 l of the rinse solution, spun and dried in air at room temperature hanging on a line. The treated terry cotton hand towels were then cut into 10 equal pieces measuring 16 cm×25 cm and distributed to a group of 9 subjects who evaluated the softness feel on a scale ranging from 0 points for hard and unpleasant to the touch to 5 points for soft and pleasant to the touch. Here, in each case 2 compositions were assessed in comparison with Rewoquat WE18 (methyltriethanolammonium methylsulphate ditallow fatty acid ester) and an untreated piece of terry cotton hand towel. The value given in the examples for the softness feel is the sum of the points awarded for the composition divided by the sum of the points awarded for Rewoquat WE18, multiplied by 100. Values of more than 100 accordingly mean a better softness feel than with Rewoquat WE18 and values of less than 100 mean a poorer softness feel. Repeat experiments showed that differences in the softness feel of more than 10 are statistically significant.

In the examples, Cx refers in each case to a fatty acid radical or fatty alkyl radical having x carbon atoms, where C18:1 refers to a monounsaturated oleyl radical. DMEA-Quat-Cx denotes a trimethylethanolammonium methylsulphate fatty acid ester of a fatty acid having x carbon atoms, DMIPA-Quat-Cx the corresponding trimethyl-(2-propanol) ammonium methylsulphate fatty acid ester and DMAPA-Quat-Cx the corresponding trimethyl-(3-aminopropyl) ammonium methylsulphate fatty acid amide. All quaternary ammonium salts (DMEA-Quats, DMIPA-Quats, DMAPA-Quats and Rewoquat WE18) in each case comprised 15% by weight 2-propanol.

TABLE 1

Compositions with fatty acid as nonionic compound

| Example | Ammonium salt A | Fatty acid B | A:B molar ratio | Softness feel |
|---|---|---|---|---|
| 1* | DMEA-Quat-C18 | C12 | 1:1 | 45 |
| 2* | DMEA-Quat-C18 | C14 | 1:1 | 54 |
| 3 | DMEA-Quat-C18 | C16 | 1:1 | 95 |
| 4 | DMEA-Quat-C18 | C18 | 1:1 | 124 |
| 5* | DMEA-Quat-C18 | C18:1 | 1:1 | 51 |
| 6* | DMEA-Quat-C18:1 | C18:1 | 1:1 | 39 |
| 7 | DMIPA-Quat-C18 | C18 | 1:1 | 94 |
| 8 | DMAPA-Quat-C18 | C18 | 1:1 | 76 |

*not according to the invention

TABLE 2

Compositions with fatty alcohol as nonionic compound

| Example | Ammonium salt A | Fatty alcohol B | A:B molar ratio | Softness feel |
|---|---|---|---|---|
| 9* | DMEA-Quat-C18 | C12 | 1:1 | 39 |
| 10 | DMEA-Quat-C18 | C18 | 1:1 | 95 |
| 11 | DMEA-Quat-C18 | C18 | 3:2 | 73 |
| 12* | DMEA-Quat-C18 | C18 | 7:3 | 43 |
| 13 | DMAPA-Quat-C18 | C18 | 1:1 | 55 |
| 14* | DMAPA-Quat-C18:1 | C18:1 | 1:1 | 40 |

*not according to the invention

TABLE 3

Compositions with glycerol fatty acid monoester as nonionic compound

| Example | Ammonium salt A | Glycerol fatty acid monoester B | A:B molar ratio | Softness feel |
|---|---|---|---|---|
| 15* | DMEA-Quat-C12 | C12 | 1:1 | 25 |
| 16* | DMEA-Quat-C18 | C12 | 1:1 | 28 |
| 17* | DMEA-Quat-C12 | C18 | 1:1 | 50 |
| 18* | DMEA-Quat-C14 | C18 | 1:1 | 61 |
| 19 | DMEA-Quat-C16 | C18 | 1:1 | 73 |
| 20 | DMEA-Quat-C18 | C18 | 1:1 | 100 |
| 21* | DMEA-Quat-C18 | C18:1 | 1:1 | 51 |
| 22* | DMEA-Quat-C18:1 | C18 | 1:1 | 75 |
| 23* | DMEA-Quat-C18:1 | C18:1 | 1:1 | 51 |
| 24* | DMEA-Quat-C18 | C18 | 1:4 | 75 |
| 25 | DMEA-Quat-C18 | C18 | 3:7 | 88 |
| 26 | DMEA-Quat-C18 | C18 | 2:3 | 88 |
| 27 | DMEA-Quat-C18 | C18 | 3:2 | 94 |
| 28* | DMEA-Quat-C18 | C18 | 7:3 | 72 |
| 29* | DMEA-Quat-C18 | C18 | 4:1 | 58 |
| 30 | DMIPA-Quat-C18 | C18 | 1:1 | 79 |
| 31* | DMAPA-Quat-C12 | C12 | 1:1 | 30 |
| 32* | DMAPA-Quat-C12 | C18 | 1:1 | 61 |
| 33 | DMAPA-Quat-C18 | C18 | 1:1 | 83 |
| 34 | DMEA-HOAc** | C18 | 1:1 | 113 |

*not according to the invention
**Dimethylethanolammonium acetate stearic acid ester

TABLE 4

Compositions with triglycerol fatty acid monoester as nonionic compound

| Example | Ammonium salt A | Triglycerol fatty acid monoester B | A:B molar ratio | Softness feel |
|---|---|---|---|---|
| 35 | DMEA-Quat-C18 | C18 | 1:1 | 81 |
| 36 | DMEA-Quat-C18 | C16/18* | 1:1 | 80 |

*Mixture of palmitic acid and stearic acid

TABLE 5

Composition with sorbitan fatty acid monoester as nonionic compound

| Example | Ammonium salt A | Sorbitan fatty acid monoester B | A:B molar ratio | Softness feel |
|---|---|---|---|---|
| 37 | DMEA-Quat-C18 | C16/18* | 1:1 | 89 |

*Mixture of palmitic acid and stearic acid

TABLE 6

Compositions with fatty acid ethoxylate, fatty alcohol ethoxylate or fatty acid methyl ester as nonionic compound

| Example | Ammonium salt A | Nonionic compound B | A:B molar ratio | Softness feel |
|---|---|---|---|---|
| 38* | DMEA-Quat-C18 | C18-fatty acid diethoxylate | 1:1 | 57 |
| 39* | DMAPA-Quat-C18:1 | C18:1-fatty acid diethoxylate | 1:1 | 54 |
| 40* | DMEA-Quat-C18 | C18-fatty alcohol diethoxylate | 1:1 | 65 |
| 41* | DMEA-Quat-C18 | C18-fatty acid methyl ester | 1:1 | 66 |

*not according to the invention

Example 42

Not According to the Invention

Example 4 of EP 0 284 036 A2 was reworked and the resulting product was analyzed with $^1$H and $^{13}$C-NMR. The resulting composition comprised 58 mol % choline chloride stearic acid ester (component A), 15 mol % choline chloride, 10 mol % glycerol 1-stearate (component B), 5 mol % glycerol, 4 mol % glycerol 1,3-distearate, 3 mol % glycerol tristearate, 2 mol % glycerol 1,2-distearate and 2 mol % stearic acid (component B). This results in a molar ratio of the total amount of component A to the total amount of component B of 58:12, corresponding to 4.8:1. A softness feel of 64 was determined for the composition.

Example 43

Not According to the Invention

Example 1 of EP 0 284 036 A2 was reworked and the resulting product was analyzed with $^1$H and $^{13}$C-NMR. The resulting composition comprised 7.5 mol % N,N-dimethyldiethanolammonium chloride stearic acid diester, 38.3 mol % N,N-dimethyldiethanolammonium chloride stearic acid monoester (component A), 12.0 mol % N,N-dimethyldiethanolammonium chloride, 5.7 mol % glycerol tristearate, 15.4 mol % glycerol distearate, 14.8 mol % glycerol monostearate (component B) and 6.3 mol % glycerol. This results in a molar ratio of the total amount of component A to the total amount of component B of 2.6. A softness feel of 82 was determined for the composition.

Example 44

Not According to the Invention

Example 2 of EP 0 284 036 A2 was reworked and the resulting product was analyzed with $^1$H and $^{13}$C-NMR. The resulting composition comprised 39 mol % N-butyl-N-methyldiethanolammonium chloride stearic acid monoester (component A), 11 mol % N-butyl-N-methyldiethanolammonium chloride, 11 mol % N-butyl-N-methyldiethanolamine stearic acid diester, 17 mol % N-butyl-N-methyldiethanolamine stearic acid monoester, 6 mol % glycerol tristearate, 13 mol % glycerol distearate, 15 mol % glycerol monostearate (component B) and 7 mol % glycerol. This results in a molar ratio of the total amount of component A to the total amount of component B of 2.6. A softness feel of 73 was determined for the composition.

Example 45

Not According to the Invention

Example 3 of EP 0 284 036 A2 was reworked and the resulting transesterification product was analyzed with $^1$H and $^{13}$C-NMR. The transesterification product comprised 8.6 mol % triethanolamine stearic acid diester, 32.7 mol % triethanolamine stearic acid monoester, 21.8 mol % triethanolamine, 10.6 mol % glycerol tristearate, 8.9 mol % glycerol distearate, 8.9 mol % glycerol monostearate and 4 mol % glycerol. For the degree of quaternization of 95% disclosed in EP 0 284 036 A2, a content of N-methyltriethanolammonium chloride stearic acid monoester of at least 29.5 mol % and thus a molar ratio of the total amount of component A to the total amount of component B of more than 3.3 is calculated for the product of the quaternization. However, the degree of quaternization disclosed in EP 0 284 036 A2 could never be reproduced in the reworking. A softness feel of 76 was determined for the quaternized composition obtained in the reworking.

Example 46

568 g (2.02 mol) of stearic acid, 108 g (1.21 mol) of N,N-dimethylethanolamine and 93 g (1.01 mol) of glycerol are charged to an electrically heated reactor with mechanical stirrer, internal thermometer and attached rectification column, and heated to 175° C. with stirring. At this temperature, water is distilled off with stirring over 8 h. The resulting mixture is cooled to 60° C. and, with stirring, 119.7 g (0.95 mol) of dimethyl sulphate are added slowly such that the temperature does not exceed 80° C. The resulting mixture is stirred for 1 h at 80° C. and admixed with 129 g of 2-propanol. The resulting composition was analyzed with $^1$H and $^{13}$C-NMR and comprised, without taking into consideration 2-propanol, 28 mol % choline methyl sulphate stearic acid ester (component A), 17 mol % choline methylsulphate, 21 mol % glycerol 1-stearate (component B), 8 mol % glycerol 2-stearate (component B), 8 mol % glycerol 1,3-distearate, 5 mol % glycerol 1,2-distearate, 4 mol % N,N-dimethylethanolamine stearate, 3 mol % stearic acid (component B), 2 mol glycerol tristearate and 2 mol % methyl stearate. This results in a molar ratio of the total amount of component A to the total amount of component B of 28:32, corresponding to 1:1.1. A softness feel of 94 was determined for the composition.

Examples 47 and 48

Comparative Examples

Example 20 was repeated, however, no mixture of choline methylsulphate stearic acid ester and glycerol monostearate was used to produce the 5% by weight aqueous dispersion, but, in Example 47, firstly the glycerol monostearate was dispersed in the water and only thereafter was the choline methylsulphate stearic acid ester dispersed and, in Example 48, firstly the choline methylsulphate stearic acid ester was dispersed in the water and only thereafter was the glycerol monostearate dispersed. A softness feel of 86 was determined for the dispersion from Example 47 and a softness feel of 72 was determined for the dispersion from Example 48.

Experiments 47 and 48 show that by using a composition according to the invention for producing an aqueous rinse cycle fabric softener as opposed to producing the rinse cycle fabric softener from the individual components ammonium salt and nonionic softener, a rinse cycle fabric softener with an improved softening effect is obtained.

The invention claimed is:
1. A fabric softening composition, comprising:
a) as component A, at least one tertiary or quaternary ammonium salt, selected from compounds of formulae (I) and (II):

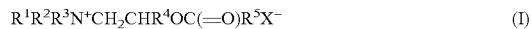

$$R^1R^2R^3N^+CH_2CHR^4OC(=O)R^5X^- \quad (I)$$

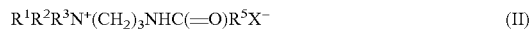

$$R^1R^2R^3N^+(CH_2)_3NHC(=O)R^5X^- \quad (II)$$

wherein:
$R^1$ is hydrogen, methyl or ethyl,
$R^2$ and $R^3$, independently of one another, are a $C_{1-4}$ alkyl or $C_{2-4}$ hydroxyalkyl,
$R^4$ is hydrogen or methyl,
$R^5$ is a linear $C_{15-21}$ alkyl or alkenyl radical and
$X^-$ is a monovalent anion,
and
b) as component B, at least one nonionic softener selected from the group consisting of fatty acids, monoesters of fatty acids with a $C_{2-6}$ diol or $C_{3-9}$ polyol, and monoesters of fatty alcohols with a $C_{2-6}$ hydroxycarboxylic acid,
and wherein:
i) the molar ratio of the total amount of component A to the total amount of component B is in the range from 2:1 to 1:3,
ii) the difference between the average chain length of the long-chain hydrocarbon radicals of components A and B is at most 2 carbon atoms,
iii) the hydrocarbon radicals of components A and B have on average in each case at most 0.5 double bonds per hydrocarbon radical and
iv) the total amount of tertiary and quaternary ammonium salts carrying two long-chain hydrocarbon radicals of 15 to 21 carbon atoms in the composition is at most 80 mol % of the total amount of components A;
v) wherein the total fraction of component A and component B in the composition is at least 50% by weight.
2. The fabric softening composition of claim 1, wherein the total amount of tertiary and quaternary ammonium salts carrying two long-chain hydrocarbon radicals of 15 to 21 carbon atoms in the composition is at most 50 mol % of the total amount of components A.
3. The fabric softening composition of claim 1, wherein the total fraction of component A and component B in the composition is at least 80% by weight.
4. The fabric softening composition of claim 1, comprising at most 10% by weight of water.
5. The fabric softening composition of claim 1, wherein component B is selected from the group consisting of fatty acids and fatty acid monoesters of glycerol, diglycerol, triglycerol, sorbitol and sorbitan.
6. The fabric softening composition of claim 1, wherein, in formulas (I) and (II), $R^2$ is a $C_{1-4}$ alkyl radical.
7. The fabric softening composition of claim 6, wherein, in formulas (I) and (II), $R^2$ is a methyl radical.
8. The fabric softening composition of claim 1, wherein in formulas (I) and (II), $R^2$ and $R^3$, independently of one another, are $C_{1-4}$ alkyl radicals.
9. The fabric softening composition of claim 8, wherein in formulas (I) and (II), $R^2$ and $R^3$ are methyl radicals.

10. The fabric softening composition of claim 1, wherein $R^1$ is methyl, in formula (I) $R^2$ and $R^3$, independently of one another, are methyl, 2-hydroxyethyl or 2-hydroxypropyl, in formula (II) $R^2$ and $R^3$ are methyl, and $X^-$ is chloride or methylsulphate.

11. The fabric softening composition of claim 1, wherein component A and component B comprise the same long-chain hydrocarbon radical.

12. An aqueous rinse cycle fabric softener comprising 70 to 98% by weight of water and 2 to 25% by weight of the fabric softening composition of claim 1.

13. A method of producing an aqueous rinse cycle fabric softener, comprising adding the composition of claim 1 in liquid form to water or an aqueous solution.

14. A process for producing the fabric softening composition of claim 1, comprising:
   a) reacting a mixture comprising
      n mol of a $C_{16-22}$ fatty acid with an iodine number of at most 45,
      m mol of a $C_{2-6}$ diol or $C_{3-9}$ polyol and
      p mol of an alkanolamine of the formula $R^2R^3NCH_2CHR^4OH$, in which $R^2$ and $R^3$, independently of one another, are methyl, 2-hydroxyethyl or 2-hydroxypropyl and $R^4$ is hydrogen or methyl,
      where the ratio of p:m is in the range from 2:1 to 1:3 and n:(p+m) is in the range from 0.75 to 1.4,
      at a temperature in the range from 140 to 210° C. with removal of water and
   b) reacting the mixture obtained in step a) with either
      i) an alkylating agent at a temperature in the range from 50 to 100° C. until at least 90% of the tertiary amino groups have been quaternized; or
      ii) an acid until at least 98% of the tertiary amino groups have been protonated.

15. The process of claim 14, wherein in step b), the mixture obtained in step a) is reacted with an alkylating agent at a temperature in the range from 50 to 100° C. until at least 90% of the tertiary amino groups have been quaternized and said alkylating agent is either dimethyl sulphate or methyl chloride.

16. The process of claim 14, wherein in step b), the mixture obtained in step a) is reacted with an acid until at least 98% of the tertiary amino groups have been protonated and said acid is a carboxylic acid having 1 to 3 carbon atoms.

17. A process for producing the fabric softening composition of claim 1, comprising:
   a) reacting a mixture comprising:
      n mol of a $C_{16-22}$ fatty acid with an iodine number of at most 45,
      m mol of a $C_{2-6}$ diol or $C_{3-9}$ polyol and
      p mol of N,N-dimethyl-1,3-propanediamine,
      where the ratio of p:m is in the range from 2:1 to 1:3 and n is in the range from 0.75*m+p to 1.4*m+p,
      at a temperature in the range from 140 to 210° C. with removal of water and
   b) reacting the mixture obtained in step a) with either:
      i) an alkylating agent at a temperature in the range from 50 to 100° C. until at least 90% of the tertiary amino groups have been quaternized; or
      ii) an acid until at least 98% of the tertiary amino groups have been protonated.

18. The process of claim 17, wherein in step b), the mixture obtained in step a) is reacted with an alkylating agent at a temperature in the range from 50 to 100° C. until at least 90% of the tertiary amino groups have been quaternized and said alkylating agent is either dimethyl sulphate or methyl chloride.

19. The process of claim 17, wherein in step b), the mixture obtained in step a) is reacted with an acid until at least 98% of the tertiary amino groups have been protonated and said acid is a carboxylic acid having 1 to 3 carbon atoms.

* * * * *